United States Patent [19]

McNeely

[11] 4,405,738

[45] Sep. 20, 1983

[54] FLAME RETARDANT ADDITIVES AND FLAME RETARDANT POLYESTER COMPOSITIONS

[75] Inventor: Gerald W. McNeely, Arden, N.C.

[73] Assignee: Akzona Incorporated, Asheville, N.C.

[21] Appl. No.: 354,981

[22] Filed: Mar. 5, 1982

[51] Int. Cl.³ .......................... C08K 5/51; C08L 85/02
[52] U.S. Cl. ................................ 524/116; 260/927 N; 525/437; 528/158; 528/399; 564/13
[58] Field of Search ................... 260/927 N; 524/116; 525/437; 528/158, 399; 564/13

[56] References Cited

U.S. PATENT DOCUMENTS

| | | | |
|---|---|---|---|
| 2,437,232 | 3/1948 | Rothrock, Jr. et al. | 528/287 |
| 2,465,319 | 3/1949 | Whinfield et al. | 526/71 |
| 2,739,947 | 3/1956 | Billica et al. | 252/471 |
| 2,744,089 | 5/1956 | Caldwell | 528/275 |
| 2,853,517 | 9/1958 | Fitzgerald et al. | 564/13 |
| 2,891,915 | 6/1959 | McCormack et al. | 528/400 |
| 2,901,466 | 8/1959 | Kibler et al. | 528/288 |
| 3,018,262 | 1/1962 | Schroeder | 427/386 |
| 3,018,272 | 1/1962 | Griffing et al. | 528/293 |
| 3,096,358 | 7/1963 | Horn | 260/429.7 |
| 3,131,207 | 4/1964 | Ratz | 260/927 N |
| 3,193,367 | 7/1965 | Stephens et al. | 65/70 |
| 3,280,222 | 10/1966 | Kober et al. | 260/927 N |
| 3,304,350 | 2/1967 | Kober et al. | 260/973 |
| 3,316,330 | 4/1967 | Nichols | 260/927 N |
| 3,322,859 | 5/1967 | Sherr et al. | 524/119 |
| 3,356,769 | 12/1967 | Allcock | 260/927 R |
| 3,370,020 | 2/1968 | Allcock et al. | 528/168 |
| 3,392,214 | 7/1968 | Jaszka | 260/927 N |
| 3,406,152 | 10/1968 | Koller | 528/275 |
| 3,433,770 | 3/1969 | Shima et al. | 526/71 |
| 3,446,763 | 5/1969 | Okuzumi | 524/711 |
| 3,450,799 | 6/1969 | Kober et al. | 260/927 N |
| 3,457,196 | 7/1969 | Herring et al. | 260/927 N |
| 3,505,087 | 4/1970 | Godfrey | 106/18.16 |
| 3,515,688 | 6/1970 | Rose | 528/399 |
| 3,624,024 | 11/1971 | Caldwell et al. | 524/281 |
| 3,629,365 | 12/1971 | Gardner | 524/139 |
| 3,711,542 | 1/1973 | Hook et al. | 564/13 |
| 3,732,316 | 5/1973 | Lin | 568/14 |
| 3,762,833 | 11/1973 | Rose et al. | 415/136 |
| 3,792,117 | 2/1974 | Kolodchin et al. | 523/506 |
| 3,856,712 | 12/1974 | Reynard et al. | 528/399 |
| 3,859,249 | 1/1975 | McNeely | 524/708 |
| 3,865,783 | 2/1975 | Clutter | 524/116 |
| 3,895,946 | 7/1975 | Huffman | 430/302 |
| 3,928,463 | 12/1975 | Reuter et al. | 260/465.1 |
| 3,974,242 | 8/1976 | Lanier et al. | 260/927 N |
| 3,996,312 | 12/1976 | Kolich et al. | 260/927 N |
| 4,005,171 | 1/1977 | Reynard et al. | 423/300 |
| 4,020,110 | 4/1977 | Lippsmeier et al. | 568/14 |
| 4,026,964 | 5/1977 | Kolich et al. | 523/506 |
| 4,029,634 | 6/1977 | Meredith | 260/927 N |
| 4,042,561 | 8/1977 | DeEdwardo et al. | 524/122 |
| 4,055,520 | 10/1977 | Dieck et al. | 521/95 |
| 4,079,035 | 3/1978 | Brackenridge | 524/116 |
| 4,094,856 | 6/1978 | Guschl | 260/927 N |
| 4,182,836 | 1/1980 | Hergenrother | 528/399 |
| 4,330,461 | 5/1982 | Mrowca | 524/100 |

FOREIGN PATENT DOCUMENTS 1208748  10/1970  United Kingdom.

OTHER PUBLICATIONS

Chem. Abstracts, 77: 115968d (Japanese Appln. 69 6177)
Allcock, Chem. & Eng. News Apr. 22, 1968, pp. 68–81.
Shaw et al., Chemical Reviews, 62: 247–281, (1962).
Haber et al., J.A.C.S., 80: 2116–2117 (1958).
Herring et al., Inorgan. Chem., 3: 428–430 (1964).
Paciorek et al., Inorgan. Chem., 3: 594–595 (1964).
"Nitrogen–Phosphorous Compounds," Academic Press, NY, NY, 1972, by Allcock Not Enclosed.
"Poly(Organophosphazenes)" Chemtech, Sep. 19, 1975, by Allcock, Not Enclosed.
Ratz et al., J.A.C.S., 84: 551–555 (1962).
Allcock, J.A.C.S., 85: 4050–4051 (1963).
Matuszko et al., J. Org. Chem., 31: 2004–2005 (1966).
Richard et al., J. Org. Chem., 28: 123–125 (1963).
Ranganathan et al., Inorg. Chem., 12: 316–319 (1973).
Evans, J.A.C.S., 101:1: 242 (1979).
Allcock et al., Inorg. Chem., 19: 1026–1030 (1980).

Primary Examiner—John Kight, III
Assistant Examiner—R. A. White
Attorney, Agent, or Firm—Francis W. Young; Jack H. Hall; H. Walter Haeussler

[57] ABSTRACT

Polyester polymers and copolyester polymers incorporating flame retardant amounts of cyclotri (or tetra) phosphazenes. These cyclotri (or tetra) phosphazenes can be added at the start of ester interchange, prior to, for example polycondensation and conventional melt spinning, or if desired, after polycondensation but before melt spinning. Specific examples of cyclotriphosphazenes and cyclotetraphosphazenes are hexa(dialkylphosphinylmethyleneoxy)cyclotriphosphazene, octa(dialkylphosphinylmethyleneoxy)cyclotetraphosphazene, tris(alkylphosphinyldimethyleneoxy)cyclotriphosphazene, tetra(alkylphosphinyldimethyleneoxy)cyclotetraphosphazene, hexa(dialkylphosphinylmethylene)cyclotriphosphazene, and octa(dialkylphosphinylmethylene)cyclotetraphosphazene.

23 Claims, No Drawings

FLAME RETARDANT ADDITIVES AND FLAME RETARDANT POLYESTER COMPOSITIONS

BACKGROUND OF THE INVENTION

It has been known to utilize various phosphorous containing materials as additives to polyester polymers to provide fire retardancy. For practical utility, however, it is not only necessary that the polymer composition be fire retardant, but it is also necessary that the polymer composition can be processed into various sized fiber and/or filament, that the product be readily dyeable and that the additive remain in the processed product during its useful life. Many of the phosphorous containing materials heretofore employed to render polyester compositions fire retardant have had phosphorous contents of about 14% or less, thus relatively large amounts of the phosphorous containing materials were necessarily employed to obtain acceptable flame retardance. In addition, perhaps because of relatively low melting points it has been observed that in some instances phosphorous containing materials were lost from fiber or filament during normal processing at elevated temperatures.

It is pointed out that certain cyclophosphazene phenyl and phenoxy derivatives and their use as fire retardant additives in polyester fibers and filaments are described in U.S. Pat. Nos. 3,865,783 and 3,859,249. In addition, Japanese application 69 6177, *Chem. Abstracts*, 77:115968d teaches there was a triphosphonitrilehexakis(di-Na phosphoxyethylamide) and the like as a textile fire resistant treatment.

The preparation and characterization of various phosphazene additives and/or chemistry that can be used or adapted for use in the practice of this invention are presented in, for example, *Chemical & Engineering News*, Apr. 22, 1968, pages 68–81 (H. R. Allcock) and U.S. Pat. Nos. 3,304,350; 3,732,316; 3,928,463 and 4,020,110. The preparation of certain organophosphorous polymers and their use as flame retardants is set forth in the following representative art U.S. Pat. Nos. 2,891,915; 3,193,397; British Pat. No. 1,208,748; *Chemical Reviews*, 62: 247–281 (1962); *J.A.C.S.*, 80: 2116 (1958) and *Inorg. Chem.*, 3: 428 & 594 (1964); see also the art cited therein, i.e. U.S. Pat. Nos. 2,853,517; 3,280,222; 3,316,330; 3,322,859; 3,356,769; 3,392,214; 3,450,799; 3,446,763; 3,505,087; 3,624,024; 3,629,365 and 3,792,117.

Polyphosphazene polymers containing repeating

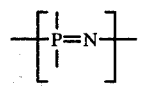

units in which various substituted and unsubstituted alkoxy, aryloxy, amino and mercapto groups are attached to the phosphorus atom and their method of preparation are described in the prior art as illustrated in the publication "Nitrogen-Phosphorus Compounds", Academic Press, New York, N.Y., 1972 by H. R. Allcock and "Poly(Organophosphazenes)", Chemtech, Sept. 19, 1975 by H. R. Allcock and in such U.S. Pat. Nos. as 3,515,688; 3,702,833; 3,856,712; 3,974,242, and 4,042,561 the disclosures of which are herein incorporated by reference.

DESCRIPTION OF THE INVENTION

Polyester polymers and copolyester polymers are made flame retardant by incorporating therein flame retardant additives which are cyclotri(or tetra)phosphazene of the formulas A, B, or C, hereinafter. These cyclotri(or tetra)phosphazenes can be added at the start of ester interchange, prior to, for example polycondensation and conventional melt spinning, or if desired, after polycondensation but before melt spinning.

Specific cyclotriphosphazenes and cyclotetraphosphazenes that can be utilized in polyester polymer to impart flame retardant properties thereto include the following:

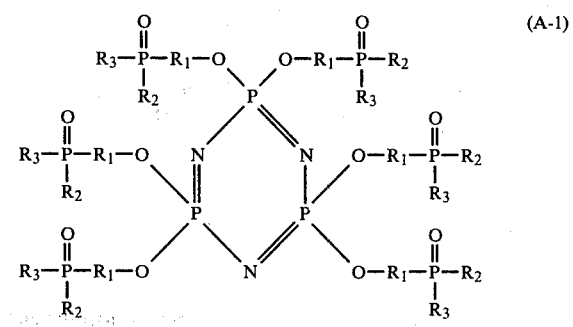
(A-1)

hexa(dialkylphosphinylmethyleneoxy)cyclotriphosphazene

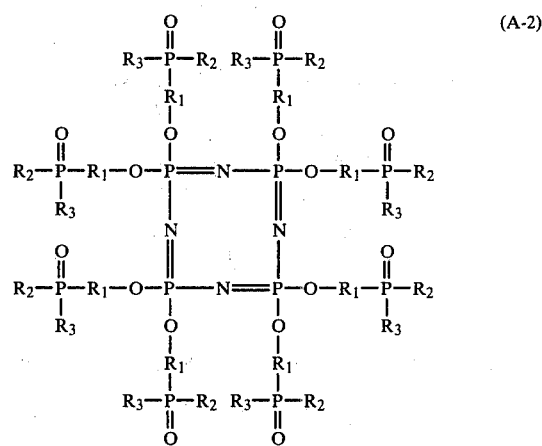
(A-2)

octa(dialkylphosphinylmethyleneoxy)cyclotetraphosphazene

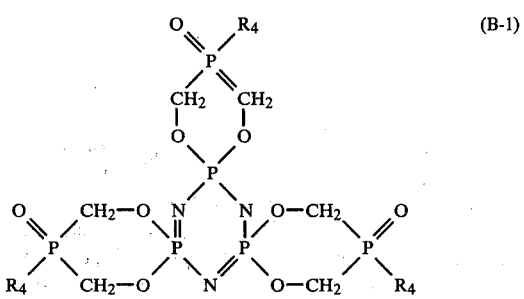
(B-1)

tri(alkylphosphinyldimethyleneoxy)cyclotriphosphazene

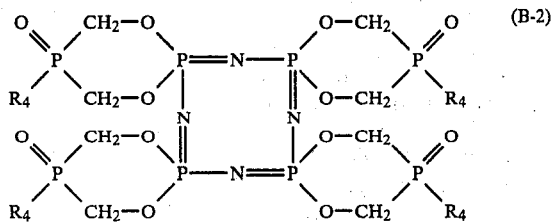

tetra(alkylphosphinyldimethyleneoxy)cyclotetraphosphazene

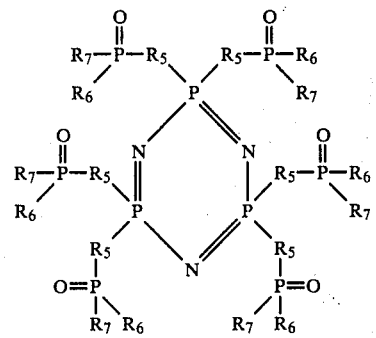

hexa(dialkylphosphinylmethylene)cyclotriphosphazene

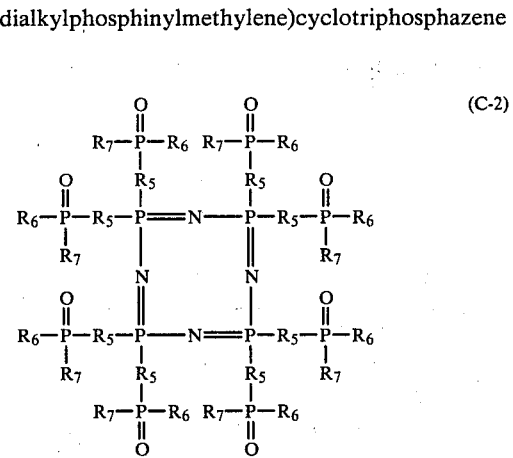

octa(dialkylphosphinylmethylene)cyclotetraphosphazene

The compounds of Formula A can be formed by the following reaction scheme:

U.S. Pat. Nos. 3,928,463 and 3,732,316, incorporated by reference, teach the preparation of hydroxymethyl phosphine oxides, i.e.

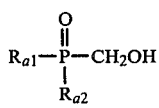

where $R_{a1}$ and $R_{a2}$ are each independently a $C_1$–$C_4$ lower alkyl group, especially of 1 or 2 carbon atoms, which may be substituted, preferably monosubstituted especially in ω-position, by groups inert under the reaction conditions such as —CN, —$OR_x$ ($R_x$ being a $C_1$–$C_4$ lower alkyl group, especially of 1 or 2 carbon atoms, halogen, especially fluorine and/or chlorine.) It has now been discovered that these known compounds will react with trimeric or tetrameric phosphonitrilic chloride to provide the compounds of the formulas A-1 and A-2 where $R_1$ is $CH_2$ and $R_2$ and $R_3$ are independently $R_{a1}$ or $R_{a2}$ as defined above, each of $R_2$ and $R_3$ preferably being —$CH_3$, i.e.

(a-1)

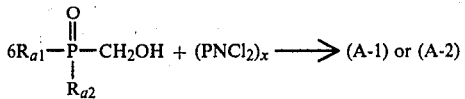

where x is 3 or 4 (see *J.A.C.S.*, 84:551–555)

It is noted that an alternative route to the starting phosphine oxides is a process related to the Arbusov reaction, i.e.

(b-2) P-$(CH_3OH)_3$ + RI → R-$P^{\oplus}(CH_2OH)_3$ $I^{\ominus}$
(b-3) R-$P^{\oplus}(CH_2OH)_3$ $I^{\ominus}$ + NaOH → R P$(CH_2OH)_2$ + NaI + CHO
(b-4)

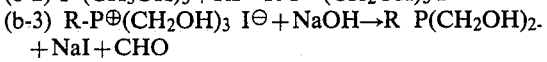

Yet further, the same general reaction scheme as directly above can be modified by employing a Grignard reaction, i.e. RMgI rather than RI.

Thus, for example, 6 moles of (hydroxymethyl)dimethylphosphine oxide can be reacted with phosphonitrilic chloride trimer or tetramer first at room temperature and then at reflux in toluene.

Generally, this reaction can be conducted at temperatures between about room temperature and about 150° C. in an inert solvent or diluent. After the reaction is complete the product is isolated by washing the reaction mixture to remove the salt and removing the inert solvent or diluent by conventional means, for example, vacuum stripping.

Alternatively, where desired, and where the phosphine oxide is otherwise stable to sodium, the sodium alcoholate of the phosphine oxide can be prepared and this metalo-organic compound reacted by slow addition to a solution or dispersion of this compound of the nitrilic chloride to provide compound A. In this case, by-product sodium chloride is removed by washing and the product is recovered from the solvent or diluent by conventional means.

EXAMPLE 1

Preparation of hexa(dimethylphosphinylmethyleneoxy)cyclotriphosphazene

Sodium hydride (60% in mineral oil), 14.4 parts is added portionwise to 64.8 parts of dimethyl hydroxymethylphosphine in 300 parts of tetrahydrofuran. After the formation of hydrogen is completed, the tetrahydrofuran is distilled and replaced with 300 parts of toluene. The resulting suspension is cooled to room temperature and a solution of 34.8 parts of hexachlorocyclotriphosphazene in toluene is added slowly. After the addition is completed, the contents of the flask are refluxed for 8 hours, cooled to room temperature and filtered to remove the NaCl. The filtrate is evaporated under reduced pressure to remove the toluene and obtain the product hexa(dimethylphosphinylmethyleneoxy)cyclotriphosphazene.

The compounds of formula (B-1 or B-2) can be formed by the following reaction scheme: U.S. Pat. No. 3,732,316, incorporated by reference, teaches the isomerization of P(CH$_2$OH)$_3$ to

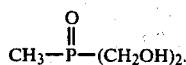

Likewise, U.S. Pat. No. 3,928,463, incorporated by reference, teaches the preparation of R$_b$-P(CH$_2$OH)$_2$ where R$_b$ can be a C$_1$-C$_4$ lower alkyl, especially of 1 or 2 carbon atoms, which may be substituted, preferably monosubstituted, especially in the ω-position, by groups inert under the reaction conditions such as —CN$_1$— OR$_x$ (R$_x$ being a C$_1$ to C$_4$ lower alkyl, especially of 1 or 2 carbon atoms) or halogen, especially fluorine and/or chlorine. It has now been discovered that these known compounds will react with trimeric or tetrameric phosphonitrilic chloride to provide the compounds of formula (B-1) or (B-2) where the R$_4$'s are each, independently, as R$_b$ is defined above and are all preferably —CH$_3$ i.e.

(b-1)

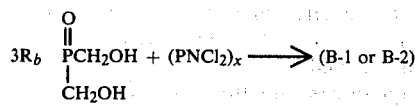

where x=3 or 4

This reaction can be carried out in art recognized procedures. For example, J.A.C.S., 85: 4050-51 (1963) teaches the reaction of catechol with phosphonitrilic chloride trimer in the presence of a halogen acceptor (e.g. a tertiary amine such as pyridine or triethylamine) to provide tris (o-phenylenedioxy) phosphonitrile. Likewise, J.O.C., 31: 2004-5 (1966) reports this phosphonitrilate compounds from ethylene glycol and 2,2-bis(nitroxymethyl) 1,3 propanediol. Further, J.A.C.S., 84: 551-555 (1962) reports the preparation of spiro polyfluorolkylene-phosphonitrilates.

Thus, for example, 3 (or 4) moles bis(hydroxymethyl)methylphosphine oxide can be reacted with phosphonitrilic chloride trimer (or tetramer) first at room temperature and then at reflux in toluene, in the presence of at least about a chlorine molar equivalency of triethylamine by slowly adding the phosphine oxide to the nitrilic chloride contained in the refluxing toluene.

Generally this reaction can be conducted at temperatures between about room temperature and about 150° C. in an inert solvent or diluent if desired, in the presence of a hydrogen halide acceptor. After the reaction is complete, the product is isolated by washing the reaction mixture to remove the salt and removing the inert solvent or diluent by conventional means, for example, vacuum stripping.

Alternatively, where desired, and where the phosphine oxide is otherwise stable to sodium, the bis sodium alcoholate can be prepared and this metaloorganic compound reacted by slow addition to a solution or dispersion of the nitrilic chloride to provide compounds (B-1) or (B-2). In this case, by-product sodium chloride is removed by washing and the product is recovered from the solvent or diluent by conventional means.

EXAMPLE 2

Preparation of tris(methylphosphinyldimethyleneoxy) cyclotriphosphazene.

To a solution of 37.2 gms. of bis(hydroxymethyl) methyl phosphine oxide in 300 ml of toluene, 30.3 gms. of triethyl amine is added. Then 34.8 gms. of hexachlorocyclotriphazene in 300 ml. of toluene is added slowly. After the addition is completed, the reaction mixture is refluxed for 18 hours. The triethylamine hydrochloride is filtered and the toluene is evaporated under reduced pressure to obtain the product, tris(methylphosphinyldimethyleneoxy) cyclotriphosphazene.

The compounds of formula (C-1) or (C-2) can be formed by the following reaction scheme:
(c-1)

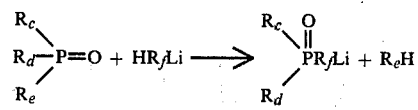

(J. Org. Chem., 28, 123-125 (1963))
where R$_f$ is (CH$_2$)$_x$ where X is 1 to 8, preferably 1 and R$_c$, R$_d$, and R$_e$ are each independently lower alkyl, aryl or cycloalkyl, then
(c-2)

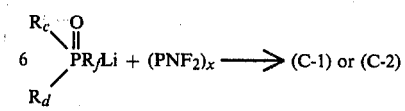

where x is 3 or 4
(See Inorg. Chem., 12(2), 316-319 (1973))
where the R$_5$'s are independently R$_f$ as defined above and R$_6$ and R$_7$ are each independently R$_c$ and R$_d$ defined above.

Alternatively, the starting alkyl lithium phosphine oxide can be prepared as follows:
(c-3)

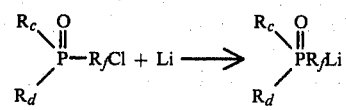

EXAMPLE 3

Preparation of Hexa(dimethylphosphinylmethylene) Cyclotriphosphazene

To 4.2 gms. of lithium metal dissolved in 100 ml of diethyl ether is added at −10° to −40° C. a solution of 75.9 gms. of dimethyl chloromethylphosphine oxide in 150 ml of diethyl ether. After the addition is completed the reaction mixture is warmed to 10° C. This solution is added slowly to a solution of 24.9 gms. of hexafluorocyclotriphosphazine in 300 ml of diethyl ether at −20° C. After the addition is completed, the reaction mixture is stirred at room temperature for 10 hours. The reaction mixture is then filtered and the filtrate is evaporated to obtain the product, hexa(dimethylphosphineylmethylene) cyclotriphosphazene.

In addition to the cyclophosphazenes described above, this invention also relates to similarly substituted open chain polyphosphazene polymers. Thus, this invention relates to polyphosphazene copolymers containing repeating

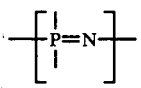

units in the polymer chain in which dialkylphosphinylmethyleneoxy, alkylphosphinyldimethyleneoxy, or dialkylphosphinylmethylene groups are attached to the phosphorus atom. Substituents groups such as alkoxy, aryloxy, amino and mercapto groups can be additionally substituted onto the polyphosphazene polymer in addition to the novel substituents by either the methods disclosed herein or by prior art methods. These polymers containing repeating units represented by the formulas:

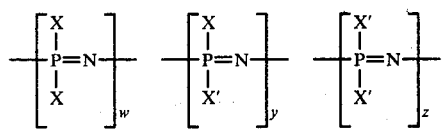

wherein X is represented by the formula:

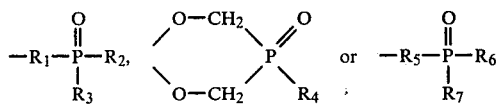

where $R_1$–$R_7$ are as defined above.

X' is X or is selected from the group consisting of substituted and unsubstituted alkoxy, aryloxy, mercapto and amino radicals, and mixtures thereof; and $20 \leq (w+y+z) \leq 50,000$ per polymer units.

As will be evident from the above formulas, in the instances where X and X' are the same, homopolymers are formed whereas where X and X' are different, copolymers are formed.

In the copolymer units represented by the above formulas, all X substituent groups can be the same or they can be mixed and all X' substituent groups can be the same or can be mixed. In the mixtures, the X substituents groups can be mixtures of different groups and the X' substituent group can be mixtures of alkoxy, aryloxy, amino and mercapto groups.

The term polymer when used in the specification will include within its meaning copolymer, that is the polyphosphazene polymer having different substitution groups in randomly substituted positions.

The polyphosphazene polymers of the invention can be represented by the formula:

[NP(X)a(X')b]n wherein n is from 20 to 50,000 and a+b=z and a and b are greater than zero.

The specific proportion of X to X' substituent groups incorporated in the polymers of the invention can vary considerably depending upon chemical and physical properties desired in the polymer and the particular end use application for which the polymer is intended. Thus, for applications such as moldings, coatings, foams and the like, the polymer should contain at least 5 mole percent by weight of the X substituent and cannot be substituted by means other than a reaction with an eth-ylenically unsaturated pendant group. The maximum percentage of X groups which can be substituted onto the polymers of the present invention can be up to about 100% or is at least about 70 mole percent by weight.

The polymers are prepared by reacting a poly(dichlorophosphazene) having the formula —(NPCl$_2$)n—, in which n is from 20 to 50,000, in the presence of a tertiary amine, with the hydroxy methyl phosphine oxides or alkali metal phosphine oxides described as reactants with the cyclic phosphazine above, alone or in admixture with any compound which is reactive under the same conditions with the poly(dichlorophosphazene) to form a substitution group on a phosphorus atom in the polyphosphazene. Examples of such compounds are discussed below.

The poly(dichlorophosphazene) polymers which are employed as starting materials in the process of this invention are well known in the art as illustrated in U.S. Pat. Nos. 3,370,020; 4,005,171; and 4,055,520 and the aforementioned publications of H. R. Allcock, the disclosures of which are incorporated herein by reference.

These polymers have the general formula —(NPCl$_2$)n—, in which n can range from 20 to 50,000 or more. As described in the aforementioned references, the polymers are in general prepared by the thermal polymerization of cyclic oligomers having the formula (NPCl$_2$)m, in which m is an integer from 3 to 7, with the cyclic trimer and tetramer often comprising up to 90% of the oligomers and the ratio of trimer to tetramer varying with the method of manufacture.

The specific conditions of temperature, pressure and time employed in the thermal polymerization of the cyclic oligomers can vary considerably depending on whether or not the polymerization is catalyzed. Thus, temperatures can range from about 130° C. to about 300° C., pressures can range from a vacuum of less than about 10$^{-1}$ Torr to superatmospheric and times can range from 30 minutes to about 48 hours.

A preferred process for preparing the poly(dichlorophosphazene) polymers used in the process of this invention is described in the aforementioned incorporated U.S. Pat. No. 4,005,171.

As indicated heretofore, the polyphosphazene copolymers of the invention in addition to the X substituent groups may contain substituted or unsubstituted alkoxy, aryloxy, amino or mercapto groups or mixtures thereof.

Preferred copolymer substituent groups include: Alkoxy groups (substituted or unsubstituted) derived from aliphatic alcohols having from 1 to 20 carbon atoms such as methanol, ethanol, propanol, isopropanol, n-butanol, sec-butanol, hexanol, jodecanol and the like; fluoroalcohols, especially those represented by the formula Z(CF$_2$)nCH$_2$OH in which Z is hydrogen or fluorine and n is an integer from 1 to 10 as illustrated by trifluoroethanol, 2,2,3,3,3-pentafluoropropanol, 2,2,3,3,4,4,4-heptafluorobutanol; 2,2,3,3-tetrafluoropropanol, 2,2,3,3,4,4,5,5-octafluoropentanol, 2,2,3,3,4,4,5,5,6,6,7,7-dodecafluoroheptanol and the like. In instances where it is desired to incorporate mixed X' substituent groups in the copolymers, mixtures of the foregoing alcohols can be employed.

Aryloxy groups (substituted or unsubstituted) derived from aromatic alcohols including among others phenol; alkylphenols such as cresols, xylenols, p-, o-, and m-ethyl and propyl phenols and the like; halogen-substituted phenols such as p-, o-, and m- chloro and bromo phenols and di- or tri-halogen substituted phenols and the like; and alkoxy-substituted phenols such as 4-methoxyphenol, 4-(n-butoxy) phenol and the like. Mixtures of the foregoing aromatic alcohols can also be employed.

Amino groups derived from any of the amino compounds heretofore employed in the polyphosphazene polymer art. Thus, the amino groups may be derived from aliphatic primary and secondary amines such as methylamine, ethylamine, dimethylamine, methylethylamine and the like and aromatic amines such as those described in U.S. Pat. No. 4,042,561, as illustrated by aniline, halogen-substituted anilines, alkyl-substituted anilines, alkoxy-substituted anilines and the like.

Mercapto groups derived from any of the mercaptan compounds heretofore employed in the polyphosphazene polymer art. Thus, for example, the mercaptan compounds described in U.S. Pat. No. 3,974,242 to Lanier et al can be utilized. Representative of suitable mercaptan compounds as described in the aforementioned patent are methyl mercaptan and its homologs ethyl, propyl, butyl, aryl and hexyl mercaptans, thiophenol, thionaphthols, benzyl mercaptan, cyclohexyl mercaptan and the like.

The use of tertiary amine in preparing the polymers of the invention where hydroxymethyl phosphine oxides are reactants minimizes undesirable side reactions and at the same time acts as an effective acid scavenger.

Tertiary amines which can be employed in preparing the polymers of the invention are those represented by the general structure:

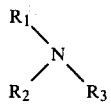

wherein $R_1$, $R_2$, and $R_3$ are alkyl containing from 1 to 8 carbon atoms. Thus, for example, the tertiary amine can be a trialkyl amine such as trimethylamine, triethylamine, tri-isopropylamine, tri-n-propylamine, tri-isobutylamine, tri-n-butylamine, and the like. In addition, tertiary amines such as pyridine and those containing diamine groups such as N,N,N',N'-tetramethylethylene diamine (TMEDA) can also be utilized.

The preferred tertiary amines for use in preparing the polymers of the invention are triethylamine, N,N,N',N'-tetramethylethylene diamine, pyridine, n-methyl morpholine, N-methyl pyrrole, 1,4-diazo-bicyclo (2.2.2) octane (DABCO) and dipiperidyl ethane.

The specific reaction conditions and the proportion of ingredients employed in preparing these polymers can vary somewhat depending on factors such as the reactivity of the specific hydroxymethyl phosphine oxide utilized, the reactivity of the compound or compounds used to form copolymer substituents, if present, the particular tertiary amine employed, and the degree of substitution desired in the final polymer. In general, reaction temperatures can range from about 25° C. to about 200° C. and times can range from 3 hours up to 7 days; with lower temperatures necessitating longer reaction times and higher temperatures allowing shorter reaction times. These conditions are, of course, utilized in order to obtain the most complete reaction possible, i.e., in order to insure the complete substitution of the chlorine atoms in the polymer to corresponding X or X' groups.

The above reaction is ordinarily carried out in the presence of a solvent. The solvent employed in the reaction should be a solvent for the poly(dichlorophosphazene) polymer, hydroxymethyl phosphine oxide, the compounds from which the copolymer substituents are derived, if present, and the tertiary amine. In addition, the materials in the reaction zone should be reasonably free of water.

A mixture of the hydroxymethyl phosphine oxide and the additional reactive compound, if present, in a predetermined molar ratio is reacted with the poly(dichlorophosphazene) to form a homopolymer or a copolymer. An alternative method is the stepwise addition of the hydroxymethyl phosphine oxide and the additional reactive compound, if desired, in any order to the poly(dichlorophosphazene) using tertiary amine, as described above, in each step, to form copolymers. The avoidance of substantial amounts of water in the reaction system is necessary in order to inhibit the premature, undesired reaction of the available chlorine atoms in the chloropolymer. Examples of suitable solvents which may be employed include diglyme, triglyme, tetraglyme, cyclohexane, chloroform, dioxane, dioxolane, methylene chloride, toluene, xylene and tetrahydrofuran. The amount of solvent employed is not critical and any amount sufficient to solubilize the reaction mixture can be employed.

In general, the amount of the combined total of the hydroxymethyl phosphine oxide and the copolymer forming compounds, if present, reacted with the polychlorophosphazene polymer should be at least molecularly equivalent to the number of available chlorine atoms in the polymer being reacted. However, an excess of hydroxymethyl phosphine oxide alone, or in combination with the copolymer forming compounds be employed in order to insure complete reaction of all the available chlorine atoms.

Prior art methods of substitution of the polyphosphazene polymers as exemplified by the reaction of the sodium salt of a compound as demonstrated in U.S. Pat. No. 3,370,020 to Allcock, et al in substituting hydroxymethyl phosphine oxide can be employed in the present invention where the appropriate alkoxide can be formed. Likewise, prior art methods such as disclosed by Allcock et al can be used to partially substitute the polyphosphazene polymer with substituents other than hydroxy methyl phosphine oxides followed by the substitution of hydroxy methyl phosphine oxide derived groups on the remaining available sites using the tertiary amine process.

As to the reaction of the alkali metal phosphine oxide reacting to provide the dialkylphosphinyl methylene substituents on the poly(dichlorophosphazene), this reaction conducted in an inert solvent or diluent in the absence of interfering compounds. Thus if a copolymer containing —O—P linked substituents is contemplated, the substituents reactions should be added stepwise.

EXAMPLE 4

Preparation of $+((CH_3)_2POCH_2O)_2PN+$ polymer

Into a reactor with inert atmosphere is charged 102 millimoles of dimethyl(hydroxymethyl)phosphine oxide, 88 millimoles of triethylamine, 100 c.c. of tetrahydrofuran (THF) and 61.8 grams (46.4 millimoles) of an 8.75 percent solids solution of poly(dichlorophosphazene) in THF. The materials are heated at 80° C. for 40 hours. The triethylamine hydrochloride crystals are separated from the solution.

EXAMPLE 5

Preparation of $+((CH_3)PO(CH_2O)_2PN+$ polymer

Into a reactor with inert atmosphere is charged 51 millimoles of methyldi(hydroxymethyl)phosphine oxide, 88 millimoles of triethylamine, 100 c.c. of THF and 61.8 grams (46.4 millimoles) of an 8.75 percent solids solution of poly(dichlorophosphazene) in THF. The materials are heated at 80° C. for 40 hours. The triethylamine hydrochloride crystals are separated from the solution.

EXAMPLE 6

Preparation of $+((CH_3)_2POCH_2)_2PN+$ polymer

Into a reactor with inert atmosphere is charged 102 millimoles of dimethylphosphinylmethylene lithium, 100 c.c. of THF and 61.8 grams (46.4 millimoles) of an 8.75 percent solids solution of poly(dichlorophosphazene) in THF. The materials are heated at 80° C. for 40 hours. The lithium chloride is separated from the product.

Any such cyclophosphazenes or linear polyphosphazenes such as those specifically set forth above, which materials are incorporated into the polyester polymer in an amount from about 1 to about 20 percent by weight, can be substituted in the representative examples that follow to achieve essentially the same results with a minimum of routine experimentation as would be readily undertaken, if necessary, by one skilled in the art.

The flame retarded polyester or copolyester produced in accordance with this invention can be satisfactorily processed in the trade and, for example, successfully deep dyed by conventional dyeing procedures from an aqueous system without the use of a carrier or with the use of a lesser amount of carrier. The variety of polyester, dyes, or mixtures thereof that can be utilized is wide in scope and depends on processing conditions and desired results, all within the realm of routine experimentation.

In the practice of the present invention, conventional additives can be incorporated prior to spinning to achieve a desired result; such additives including dyeing additives, antioxidants, stabilizers, delustrants, etc., singularly or in combination.

The flame retardant additive component of the present invention will be preferably incorporated by mixing immediately prior to extrusion or spinning; it can be added, however, at esterinterchange. This control enables the avoidance of the problem resulting when certain such additives, introduced during polymerization, would normally adversely affect the processing of and/or degrade the resulting polymer, it is submitted that the results achieved represent a significant contribution to the art in providing, for example, synthetic organic polyester filaments that can be readily processed, which filaments are flame retarded and can be subsequently handled within the skill of the art to produce desired dyed fabrics and carpeting. These end use products are flame retardant as more specifically herein described. Staple, film, and sheets of flame retarded polyester can be produced.

The polyesters employed in practicing this invention include those which are well-known in the art as exemplified by U.S. Pat. Nos. 2,465,319; 2,901,466; 2,744,089; and 3,018,262. It is to be understood that the term "polyester" includes both homopolyesters and copolyesters.

In incorporating the flame retardant additive components into the polymer melt immediately prior to spinning, known means which will achieve a thorough mixing can be utilized. It is essential that moisture be reduced to an absolute minimum in the polymer, the additives separately or at a temperature below the melting point of any one of the components. The time required for effective drying to reduce moisture content can, of course, be routinely determined. Mechanical mixing will normally be utilized followed by spinning to produce flame retarded commercially accepted filaments. Flame retardant polymeric films or sheets can also be produced.

Typical polyesters which can be modified in the practice of the present invention include those set forth in U.S. Pat. Nos. 2,465,319; 2,437,232; 2,739,957; and 2,895,946. Various processes which can be utilized to prepare such polyesters are set forth for example, in U.S. Pat. Nos. 3,433,770 and 3,406,152, the latter patent also disclosing the addition of additives to control pilling.

Copolyester can be prepared from terephthalic acid or an ester forming derivative thereof and a glycol of the formula $HO(CH_2)_nOH$, wherein n is an integer of from 2 to about 10, in the presence of a dye sensitizing sulfonate containing compound, a branching agent, such as glycerol, and a dye dispersing and dye retaining aliphatic diacid or ester thereof. The particular copolyester, sulfonate containing additive, branching agent and aliphatic diacid (or ester thereof) selected singularly or in combination, is not critical.

Polyesters and copolyesters which can be modified in the practice of this invention are well-known in the art and include those of U.S. Pat. No. 3,018,272; this disclosure also sets forth sulfonate group containing compounds which can be utilized in the practice of the present invention. U.S. Pat. No. 3,096,358 sets forth additional sulfonate compounds which can be utilized in conjunction with a selected aliphatic diacid of the formula:

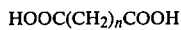

$$HOOC(CH_2)_nCOOH$$

n having a value from 2 to 18. Preferred species aliphatic diacid additives are the azelate and adipate diacids and ester derivatives thereof.

Branching agents which can be utilized include hexanetriol; pentaerythritol; trimethylolpropane, sorbitol; trimethylol ethane; glycerol; trimethylol benzene-1,3,5; tripropylol benzene-1,3,5; tributylol benzene-1,3,5; trihexylol benzene-1,2,6; trimethyl trimesate; triethyl trimesate; tripropyl trimesate; tetramethyl pyromellitate; tetramethyl mellophanate; trimethyl hemimellitate; trimethyl trimellitate and tetramethyl prehnitate.

Examples of sulfonate group containing compounds which can be utilized include metallic salts of sulfomoncarboxylic esters, sulfodicarboxylic esters, monohydric and dihydrocalcohols containing at least one sulfonic acid group and monohydric alcohols containing one carboxylic ester group and at least one sulfonic acid group.

Among the basic and disperse dyestuffs which readily dye the fibers produced from the flame retarded polyester of this invention are the "Genacryl" and "Celliton" dyes discussed on pages 432 to 433 of the American Dyestuff Reporter, volume 43, 1954, for example, Genacryl Red 6B (a basic dye of quaternary ammonium type), Genacryl Pink G. (Basic Red 13; Color Index 48015), Genacryl Blue 6G; CellitonFast Red GOA Ex. Cone (Disperse Red 17; Color Index No. 11210); Celliton Fast Blue AF Ex. Cone (Color Index No. 61115); Fuchsine SBP (a basic dye of the triphenylmethane type); Fuchsine Cone. Basic Violet 14 (Color Index No. 12510); Methyl Violet 2B; Brilliant Blue 6G; Methylene Blue SP; Victoria Green WB (Color Index 657); Victoria Green (Basic Green 4; Color Index No. 42000); Rhodamine B (Color Index 749); Brilliant Green B (Color Index 662); Sevron Brilliant Red 4G; Maxilon Red BL; Basacryl Blue GL; and the like.

Additional specific dyestuffs which can be utilized include the following:

| Dyestuff | Color Index Name |
|---|---|
| Sevron Yellow R | Basic Yellow 11 |
| Astrazon Yellow 7GLL | Basic Yellow 21 |
| Sevron Orange G | Basic Orange 21 |
| Maxilon Red BL | Basic Red 22 |
| Astrazon Red BBL | Basic Red 23 |
| Astrazon Red RL | Basic Red 25 |
| Sevron Red GL | Basic Red 18 |
| Sevron Blue ER | Basic Blue |
| Sevron Blue 5G | Basic Blue 4 |
| Sevron Blue BGL | Basic Blue 35 |
| Sevron Blue NF | Basic Blue |
| Resolin Blue FBLD | Disperse Blue 56 |
| Sevron Brilliant Red D | Basic Red 19 |

PREFERRED EMBODIMENT

In the preferred embodiment of the present invention, from 5 to about 10 weight percent hexa(dimethylphosphinylmethyleneoxy)cyclotriphosphazene is incorporated into polyester after normal ester interchange and polycondensation just prior, for example, to extrusion.

The following examples are representative and illustrate the significant utility and novelty of the present invention. The embodiments which follow are preferred and illustrate the herein described and claimed invention but are not to be construed as limiting the scope thereof.

EXAMPLE 7

Ester interchange and polycondensation procedures are routinely conducted as follows:

A. Ethylene glycol and dimethylterephthalate in a molar ratio of approximately 2.5 to 1 based on the weight of dimethylterephthalate are placed in a stirred reactor. An ester interchange catalyst, manganese acetate, in a molar ratio of 0.03-0.05 is added. The vessel is purged with nitrogen gas and then heated gradually to 210°-220° C. for 1½ to 4 hours.

During this time, methanol distilled from the reaction mixture and is collected. When the theoretical amount of methanol is collected, the prepolymer is heated for a few minutes at 215°-220° C. to insure complete reaction. The hexa(dimethylphosphinylmethyleneoxy)cyclotriphosphazene is then added.

B. The prepolymer of (A) is then mixed with the polycondensation catalyst antimony oxide. This catalyst promotes the formation of high molecular weight polyesters. A phosphorous containing stabilizer such as trimethylphosphate can also be added at this time. The vessel is flushed with nitrogen gas and heated to 280° C. with stirring. The pressure is gradually reduced to 0.2-0.5 mm. of mercury. After 1½ to 3 hours, the vacuum is broken by admitting nitrogen gas and the polyester polymer allowed to cool. The polymer is then ground, dried and spun into 30/6 yarn.

I claim:

1. A cyclopolyphosphazene selected from the group of (A) A hexa(dialkylphosphinylmethyleneoxy)cyclotriphosphazene corresponding to the formula:

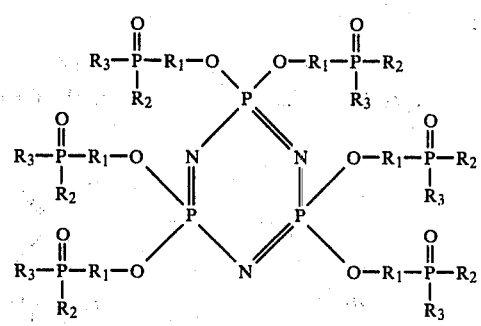

and (B) An octa(dialkylphosphinylmethyleneoxy)cyclotetraphosphazene corresponding to the formula:

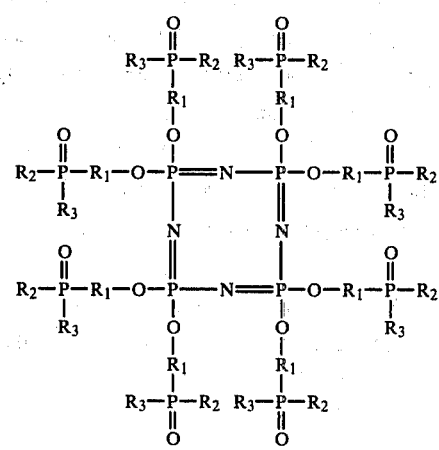

where $R_1$ is $-CH_2-$ and each $R_2$ and $R_3$ is independently a $C_1-C_4$ lower alkyl or substituted alkyl group.

2. The compound of claim 1 selected from the group consisting of hexa(dimethylphosphinylmethyleneoxy)cyclotriphosphazene and octa(dimethylphosphinylmethyleneoxy)cyclotetraphosphazene.

3. The compound of claim 1 which is hexa(dimethylphosphinylmethyleneoxy)cyclotriphosphazene.

4. A cyclopolyphosphazene selected from the group of (A) A tris(alkylphosphinyldimethyleneoxy)cyclotriphosphazene corresponding to the formula:

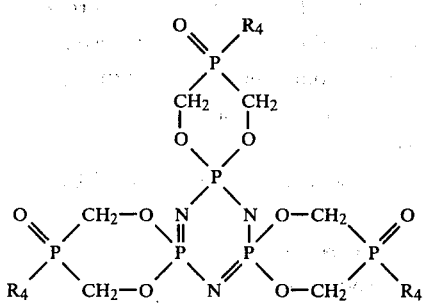

and (B) A tetra(alkylphosphinyldimethyleneoxy)cyclotetraphosphazene corresonding to the formula:

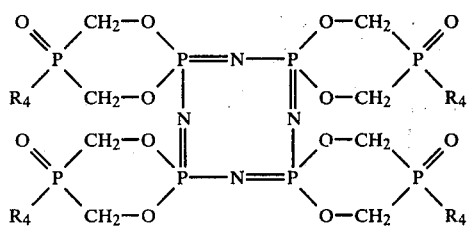

where each $R_4$ is independently a $C_1$-$C_4$ lower alkyl or substituted alkyl group.

5. The compound of claim 4 selected from the group consisting of tris(methylphosphinyldimethyleneoxy)cyclotriphosphazene and tetrakis(methylphosphinyldimethyleneoxy)cyclotetraphosphazene.

6. The compound of claim 4 which is tris(methylphosphinyldimethyleneoxy)cyclotriphosphazene.

7. A cyclopolyphosphazene selected from the group of (A) A hexa(dialkylphosphinylmethylene)cyclotriphosphazene corresponding to the formula:

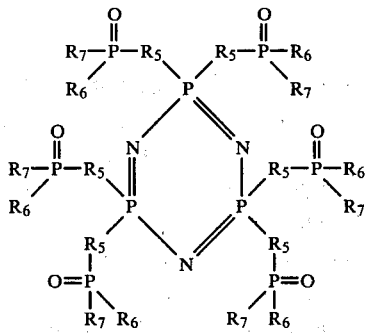

and (B) An octa(dialkylphosphinylmethylene)cyclotetraphosphazene corresponding to the formula:

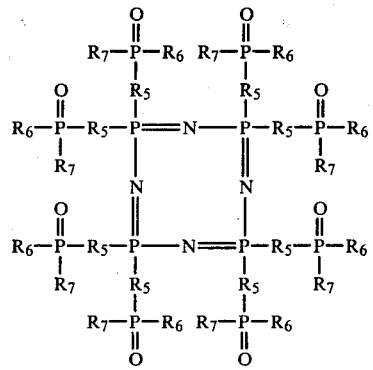

where each $R_5$ independently is $+CH_2+_x$ where X is 1 to 8 and each of $R_6$ and $R_7$ are independently lower alkyl, aryl or cycloalkyl having up to 8 carbon atoms.

8. The compound of claim 7 where $R_6$ and $R_7$ are alkyl.

9. The compound of claim 7 selected from the group consisting of hexa(dimethylphosphinylmethylene)cyclotriphosphazene and octa(dimethylphosphinylmethylene)cyclotetraphosphazene.

10. The compound of claim 7 which is hexa(dimethylphosphinylmethylene)cyclotriphosphazene.

11. A linear polyphosphazene polymer comprising units of the formulas:

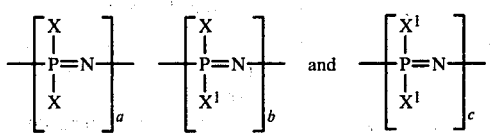

wherein X is independently

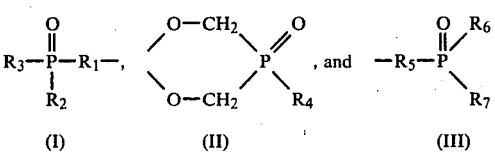

where $R_1$ is methylene and each $R_2$, $R_3$ and $R_4$ is independently a $C_1$-$C_4$ lower alkyl or substituted alkyl group; each $R_5$ is independently $+CH_2+_x$ where x is 1 to 8 and each $R_6$ and $R_7$ is independently lower alkyl, aryl or cycloalkyl having up to 8 carbon atoms;

wherein $X^1$ is selected from the group consisting of X and substituted and unsubstituted alkoxy, aryloxy, mercapto and amino radicals or mixtures thereof; and wherein a+b+c is from 20 to about 50,000.

12. The linear polyphosphazene polymer of claim 11 wherein $R_2$, $R_3$, $R_4$, $R_6$ and $R_7$ are methyl and $R_5$ is methylene.

13. The linear polyphosphazene polymer of claim 11 wherein X is (I) or (II).

14. The linear polyphosphazene polymer of claim 13 wherein $R_2$, $R_3$ and $R_4$ are methyl.

15. The linear polyphosphazene polymer of claim 11 wherein X is (I).

16. The linear polyphosphazene polymer of claim 15 wherein $R_2$ and $R_3$ are methyl.

17. The linear polyphosphazene polymer of claims 11, 12, 13, 14, 15 or 16 where $X^1$ is X.

18. Flame retarded linear polyester containing from about 1 to about 20 weight percent of a polyphosphazene as in claims 1, 2, 3, 4, 5, 6, 7, 8, 9, 10, 11, 12, 13, 14, 15, or 16.

19. The flame retarded linear polyester of claim 18 wherein said polyphosphazene is present in an amount of from about 5 to about 10 weight percent.

20. Flame retarded linear polyester containing from about 1 to about 20 weight percent of a polyphosphazene as in claims 1, 2, 3, 4, 5, 6, 7, 8, 9 or 10.

21. Flame retarded linear polyester containing from about 1 to 20 weight percent of a cyclopolyphosphazene selected from the group consisting of hexa(dimethylphosphinylmethyleneoxy)cyclotriphosphazene and octa(dimethylphosphinylmethyleneoxy)cyclotetraphosphazene.

22. Flame retarded linear polyester containing from about 1 to about 20 weight percent of a linear polyphosphazene as in claims 13, 14, 15 or 16.

23. Flame retarded linear polyester containing from about 1 to about 20 weight percent of a linear polyphosphazene as in claim 17.

* * * * *